United States Patent [19]

Giongo et al.

[11] 4,053,521
[45] Oct. 11, 1977

[54] ASYMMETRICAL HYDROGENATION BY MEANS OF OPTICALLY ACTIVE ALUMINUM HYDRIDE DERIVATIVES

[75] Inventors: Matteo Giongo, Mentana; Walter Marconi, San Donato Milanese; Nicola Palladino, Monterotondo; Francesco Di Gregorio, Milan, all of Italy

[73] Assignee: Snam Progetti S.p.A., San Donato Milanese, Italy

[21] Appl. No.: 684,487

[22] Filed: May 10, 1976

Related U.S. Application Data

[63] Continuation of Ser. No. 460,221, April 11, 1974, abandoned.

[30] Foreign Application Priority Data

Apr. 13, 1973 Italy ............................ 22954/73

[51] Int. Cl.² .................. C07C 29/14; C07C 29/00
[52] U.S. Cl. ................... 260/618 H; 260/606.5 P; 260/583 R
[58] Field of Search ................. 260/618 R, 618 H,

[56] References Cited

U.S. PATENT DOCUMENTS 3,852,262  12/1974  Vit et al. .................. 260/638 B

OTHER PUBLICATIONS

Giongo et al., Tetrahedron Letter, No. 34, pp. 3195–3198 (1973).

Primary Examiner—James O. Thomas, Jr.
Assistant Examiner—James H. Reamer
Attorney, Agent, or Firm—Morgan, Finnegan, Pine, Foley & Lee

[57] ABSTRACT

A prochiral or racemic substrate such as a prochiral ketone is converted into an optically active product through a process wherein said substrate is subjected to an asymmetric hydrogen transfer reaction by means of an optically active amino-alane or polyimino-alane represented by the formula $$H_2AlNR_1R_2, \ H\ Al(NR_1R_2)_2 \ \text{or} \ (H\ AlNR)_n$$

wherein R, R₁ and R₂ are alkyl, aryl or cycloalkyl radicals, n is an integer higher than 4, and which contains an Al — N direct bond and an Al — H bond per aluminum atom, and the third substituent bound to aluminum is halogen, —H,

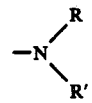

or —OR wherein R has the aforesaid meaning, and wherein the asymmetry center is constituted by a primary or secondary amine group containing an optically active alkyl radical.

3 Claims, No Drawings

ASYMMETRICAL HYDROGENATION BY MEANS OF OPTICALLY ACTIVE ALUMINUM HYDRIDE DERIVATIVES

This is a continuation of application Ser. No. 460,221 filed Apr. 11, 1974 now abandoned.

The present invention relates to the employment of monomer amino-alanes and polymer imino-alanes in the reduction of prochiral or racemic substrates in order to produce optically active products.

The synthesis of optically active compounds such as alcohols, and amines having a high degree of steric purity has become one of the most important synthesis problems both from the technical point of view and the economic point of view.

In fact the progress in recent years in obtaining natural products through partial or total synthesis has made more and more attractive the direct synthesis of optically active compounds without needing the resolution of the optical antipodes.

Up to the present the highest optical purities in an asymmetrical synthesis have generally been obtained in enzymatic or microbiological reactions, however the problems associated with the employment of such methods, in continuous reactions too, make the option of a chemical synthesis very attractive in many applications such as for instance, in the asymmetrical hydrogenations of prochiral substrates such as ketones and, imines or racemic substrates such as epoxides, and trialkylphosphinoxides in order to give the corresponding optically active alcohols and amines by means of optically active complex metal hydrides.

Up to the present the only direct or indirect asymmetrical reductions of the aforesaid substrates by means of hydrides of elements belonging to the 3rd Group of the periodic system have been reported with respect to hydrogen transfer reactions from aluminum and lithium hydride in the presence of optically active alcohols. Generally such reactions run via formation of the corresponding metal alkoxy hydrides, at low values of the optical induction and strict limitations in the choice of the reaction conditions because of the low solubility of the reagents.

The highest reported optical yields are in the range of about 45 – 50%: the optical yield is deduced from the ratio ($\alpha$) obs./($\alpha$) max. · 100.

We have now found that it is possible to perform asymmetrical reactions of hydrogen transfer from optically active aluminum hydrides at much higher optical induction values if the aluminum alkoxy-hydrides which are optically active because of the presence of an asymmetrical alkoxy group are replaced by optically active amino-alanes or polyimino-alanes of the type $$H_2AlNR_1R_2, \; H\,Al\,(NR_1R_2)_2, \; (HAlNR)_n$$

wherein R, $R_1$ and $R_2$ are alkyl, aryl or cycloalkyl radicals and $n$ is an integer higher than 4, containing at least a direct Al—N bond and an Al—H bond per aluminium atom, while the third substituent bound to the aluminium atom may be halogen, —H, —N (R)$_2$, —OR, and wherein the asymmetry centre is constituted by a primary or secondary amine group containing at least an optically active alkyl radical.

We use such derivatives in the asymmetrical hydrogenation reaction of prochiral ketones, imines, N-substituted imines, oximes, or racemic alkylenoxides and trialkylphosphine oxides to give the corresponding optically active reduced compounds at much higher optical induction values. Sometimes we obtained optical yields equal to 85%.

Their solubility in various solvents at low temperature also allows them to be employed as reducing agents under conditions wherein $AlH_3$ and $LiAlH_4$ or other hydrides do not give good results.

Amino- and imino- alanes have been prepared from optically active primary or secondary amines and from $AlH_3$·D or $LiAlH_4$ according to the reactions:

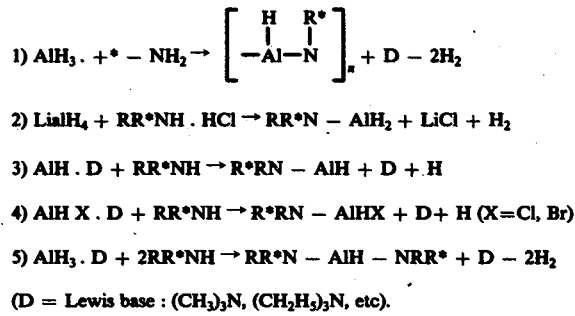

2) $LiAlH_4 + RR^*NH \cdot HCl \rightarrow RR^*N - AlH_2 + LiCl + H_2$

3) $AlH \cdot D + RR^*NH \rightarrow R^*RN - AlH + D + H$

4) $AlH\,X \cdot D + RR^*NH \rightarrow R^*RN - AlHX + D + H \;(X=Cl,\,Br)$

5) $AlH_3 \cdot D + 2RR^*NH \rightarrow RR^*N - AlH - NRR^* + D - 2H_2$ (D = Lewis base : $(CH_3)_3N$, $(CH_2H_5)_3N$, etc).

Amines may be, for instance, bornylamine, sec. butylamine, phenethylamine, menthylamine and any primary amine wherein the substituent is optically active or a secondary amine wherein at least one of the substituents is optically active such as N-methyl phenethylamine, picaline, desoxyephedrine, O-methyl ephedrine while the other substituent may be chiral or achiral. Some alanes prepared as aforesaid are reported hereinafter

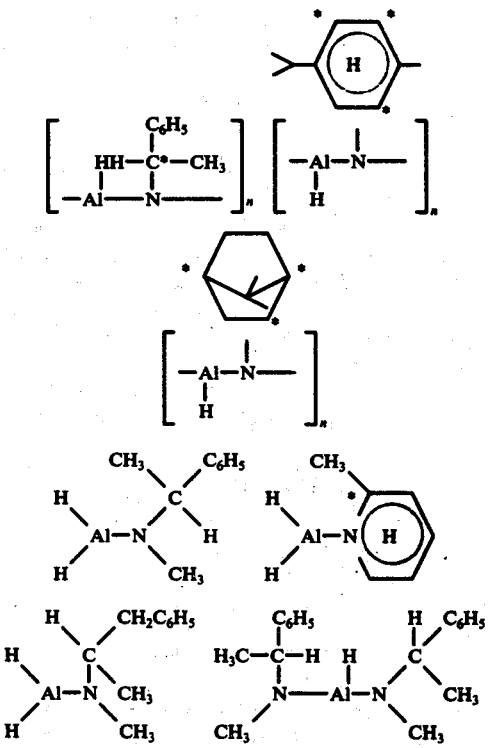

They have been employed in the reduction of prochiral substrates such as ketones, imines, oximes in various solvents and in the temperature range between +50° and −100° C according to the solvent and substrate nature.

According to the reported factors we have sometimes obtained asymmetrical induction values of 85%.

The reaction scheme is reported hereinafter

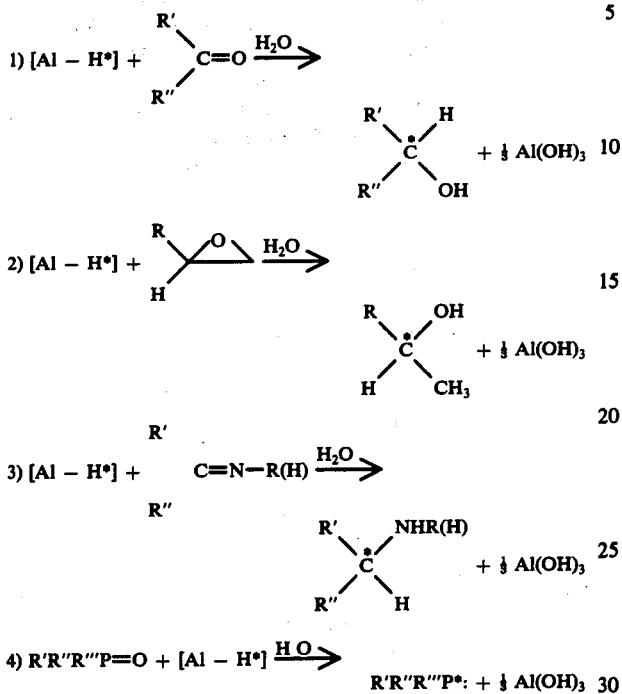

At the end of the reaction the asymmetrical amine is recovered almost completely without any measurable indication of racemization.

This fact excludes the possibility of a hydrogen transfer from the asymmetrical C atom when amine is

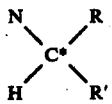

The advantage deriving from using the aminoalanes reported in this specification consists of the possibility of operating under the widest temperature conditions and in the most different solvents, in obtaining optical yields very much higher than the ones reported for other systems based on metal hydrides able to effect an asymmetrical hydrogenation reported thus far and of the almost total recovery of the agent causing the optical induction.

EXAMPLE 1

0.215 mole of acetophenone dissolved in 100 ml of ethyl ether were slowly dripped into a solution constituted by 0.11 mole of N-methyl phenethylamino-alane in 600 ml of ether cooled at 0° C. After 4 hours the solution was hydrolized with water and ice by keeping the pH $\leq$ 4 with HCl. The organic phase was separated: the aqueous phase was extracted by three portions of 100 ml of ether. The extracts, joined combined, were reduce to a small volume.

The residual oil was treated with semicarbazide, HCl and sodium acetate in water-ethanol solution ¼ at 60° C.

By diluting with very much water and cooling at 0° C we separated the unreacted acetophenone, as semicarbazone, which was filtered. The clear solution was extracted four times with 100 ml of ether. The combined extracts were dried on $Na_2SO_4$ and the solvent was evaporated.

The residue was distilled under vacuum (0.1 - 0.15 mmHg).

23.6 g of phenyl methylcarbinole were obtained (yield 90%) $[\alpha]_{D\ obs.}^{23} = -5.5°$ (optical yield 12.5).

From the hydrolis mother waters we recovered, by alkalinization, ether extraction and a gaseous HCl treatment, g 19.1 of N-methylphenethylamino.HCl (93% yield) $[\alpha]_{546\ obs.}^{23} = -29.9$ (EtOH c = 5).

The amine chlorohydrate employed in the synthesis of dialkyl amino-alane had $[\alpha]_{546}$ obs.$^{23}$ = −30.0 (EtOH, C = 5).

EXAMPLE 2

By working according to the procedure of example 1, acetophenone and N-methylphenethylaminoalane (2:1) were reacted at −73° C in ethyl ether. The corresponding carbinol was obtained at a 57.5% yield had $[\alpha]_{D\ obs.}^{23} = -37.2°$. Optical yield 85%.

EXAMPLE 3

By working according to the procedure of example 1 acetophenone and N-methylphenethylamine (2:1) were reacted at 0° C in toluene. The corresponding carbinol was obtained at a yield of 88% had $[\alpha]_{D\ obs.}^{23} = -12.04°$, optical yield = 27.4%.

EXAMPLE 4

By working according to the procedure of example 1 acetophenone and N-methylphenethylamine (2:1) were reacted at −70° C in toluene. The corresponding carbinol, obtained at a yield of 63.5%, had $[\alpha]_{D\ obs.}^{23} = -32.6°$; optical yield = 74%.

EXAMPLE 5

At −70° C 11.4 g of N(n-butyl) imino-2 butanone were added to a solution constituted by 16.3 g of N-methylphenethylamino-alane in ethyl ether. At the end of the reaction the whole was hydrolized by ice and alkali. The ether fraction was separated and the aqueous phase was again thrice extracted by ether. The ether extracts, combined, were dried on $Na_2SO_4$ and evaporated under a reduced pressure. Sec - butyl amine was obtained from the remaining oil by a fractionation at 12 mm., at a yield of 40–45% $[\alpha]_{D\ obs.}^{25} = +2.9°$ and optical yield = 18%.

EXAMPLE 6

By working according to the procedure of example 1, acetophenone and (+) picoline-alane (2:1) were reacted at −70° C in tetrahydrofuran. Corresponding carbinol, obtained at a yield of 60%, had $[\alpha]_{D\ obs.}^{23} = -9.8°$ (optical yield = 22.5%).

EXAMPLE 7

By working according to the procedure of example 1 acetophenone and poly ( (−) phenethyl) imino-alane were reacted at 0° C in ethyl ether. Corresponding carbinol, obtained at yields of 80 %, had $[\alpha]_{D\ obs.}^{23} = +4.42°$ (optical yield = 14.4%).

EXAMPLE 8

To a solution of 0.31 mole of N-methylphenethylamino-alane in benzene, at 25° C, was added a benzene solution of 3-methyl, 1-phenyl, 1-phospha, 3 cyclopentene, 1-oxide (I)

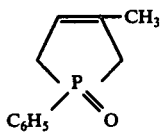

At the end of the addition the whole was kept at room temperature for three hours under stirring, then it was hydrolized by ice and alkali.

The benzene phase was extracted, dried on KOH and evaporated under reduced pressure. By a distillation at 0.1 mmHg N-metylphenethylamino was recovered ($BP_{0.1}$ = 48° C yield = 70–75%, optical purity = 98%).

The following fraction was constituted by 3-methyl 1-phenyl 1-phospha-3-cyclopentene (II)

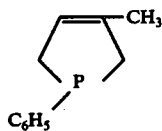

Yield = 55–60%; $[\alpha]_{D\,obs.}^{25}$ = +6.78°. The maximum specific rotation of this phosphine is not known.

EXAMPLE 9

13.2 g (0.115 mole) of i-butyl-methyl-ketoxime were slowly added, over one hour and 30 minutes, to a solution of g 20.8 (ml 0.13) of N-methylphenethylamine-alane in 250 ml of ether, at 0° C.

After the solution had been refluxed for three hours, it was hydrolized by ice. After the solution had been brought to quite alkaline pH, it was extracted by ether (100 ml for three times).

The extracts, combined and dried on solid KOH, were evaporated.

The residue was distillated at 15 mmHg. The different fractions were analyzed at G LC. Iso-butyl-methyl-amine was obtained at a yield of 50% and had $[\alpha]_{D\,obs.}^{23}$ = −0.63° (scientific papers: − 10.7°; optical yield = 5.9%). N-methylphenethylamine, as chlorohydrate, was isolated from the distillation residue at a yield of 90%. The optical purity of the recovered amine was 98% with respect to the starting value.

All measurements of the rotatory optical power were carried out on pure samples and not on diluted samples.

What we claim is:

1. A process for asymmetrically hydrogenating acetophenone to an optically active product which comprises contacting acetophenone with N-methyl phenethylamino-alane in the presence of an organic solvent at a temperature in the range of from −100° to +150° C and thereafter subjecting the reaction mixture to hydrolysis to obtain the optically active product.

2. A process for asymetrically hydrogenating acetophonone to an optically active product which comprises contacting acetophenone with (+) pipecolino-alane in an organic solvent at a temperature in the range of from −100° to +150° C and thereafter subjecting the reaction mixture to hydrolysis to obtain the optically active product.

3. A process for asymmetrically hydrogenating acetophenone which comprises contacting acetophenone with poly ( (−) phenethyl) imino alane in an organic solvent at a temperature in the range of from −100° to +150° C and thereafter subjecting the reaction mixture to hydrolysis to obtain the optically active product.

* * * * *